United States Patent
Biedermann et al.

(10) Patent No.: US 9,492,204 B2
(45) Date of Patent: Nov. 15, 2016

(54) POLYAXIAL BONE ANCHORING DEVICE WITH ENLARGED PIVOT ANGLE

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 1 day.

(21) Appl. No.: 14/539,461

(22) Filed: Nov. 12, 2014

(65) Prior Publication Data

US 2015/0142059 A1 May 21, 2015

Related U.S. Application Data

(60) Provisional application No. 61/904,403, filed on Nov. 14, 2013.

(30) Foreign Application Priority Data

Nov. 14, 2013 (EP) .................................... 13192978

(51) Int. Cl.
*A61B 17/70* (2006.01)

(52) U.S. Cl.
CPC ....... *A61B 17/7037* (2013.01); *A61B 17/7035* (2013.01)

(58) Field of Classification Search
CPC ............ A61B 17/7037; A61B 17/7035; A61B 17/7041

(Continued)

(56) References Cited

U.S. PATENT DOCUMENTS

| 9,232,969 B2 * | 1/2016 | Farris ................. A61B 17/7037 |
| 2006/0241596 A1 * | 10/2006 | Rezach .............. A61B 17/7041 606/264 |

(Continued)

FOREIGN PATENT DOCUMENTS

| EP | 2 559 390 A1 | 2/2013 |
| WO | WO 2007/130007 A1 | 11/2007 |

OTHER PUBLICATIONS

Extended European Search Report for European Application No. 13192978.8, European Search Report dated Apr. 10, 2014 and mailed Apr. 24, 2014 (7 pgs.).

*Primary Examiner* — Jan Christopher Merene
(74) *Attorney, Agent, or Firm* — Lewis Roca Rothgerber Christie LLP (57) ABSTRACT

A polyaxial bone anchoring device includes a receiving part configured to be pivotably connected to a head of an anchoring element, the receiving part having a channel for receiving a rod, an accommodation space having an opening for accommodating the head, and a passage extending from a first end of the receiving part to the accommodation space, a cap member having a first portion configured to be positioned in the accommodation space and to hold the head, wherein the first portion is expandable in the accommodation space to allow insertion of the head and compressible to exert pressure on the head, and a sleeve-like insert piece including a spherical segment-shaped outer surface portion. The insert piece can be positioned at least partially around the first portion of the cap member and can pivot in the receiving part when the cap member and the insert piece are in the receiving part.

24 Claims, 9 Drawing Sheets (58) Field of Classification Search
USPC .......................................................... 606/266
See application file for complete search history.

(56) References Cited

U.S. PATENT DOCUMENTS

| | | | |
|---|---|---|---|
| 2007/0118123 A1 | 5/2007 | Strausbaugh et al. | |
| 2008/0132957 A1* | 6/2008 | Matthis .............. | A61B 17/7032 606/301 |
| 2008/0161859 A1* | 7/2008 | Nilsson .............. | A61B 17/7032 606/266 |
| 2010/0234902 A1 | 9/2010 | Biedermann et al. | |
| 2011/0276098 A1* | 11/2011 | Biedermann ...... | A61B 17/7037 606/305 |
| 2012/0109218 A1* | 5/2012 | Farris ................ | A61B 17/7038 606/305 |
| 2012/0136395 A1 | 5/2012 | Biedermann et al. | |
| 2012/0232598 A1* | 9/2012 | Hestad ............... | A61B 17/7037 606/305 |
| 2013/0096620 A1* | 4/2013 | Biedermann .......... | A61B 17/70 606/279 |
| 2013/0110178 A1* | 5/2013 | Biedermann ...... | A61B 17/7037 606/305 |
| 2013/0144346 A1* | 6/2013 | Jackson ............. | A61B 17/8605 606/305 |
| 2014/0257411 A1* | 9/2014 | Rezach .............. | A61B 17/7037 606/305 |

* cited by examiner

POLYAXIAL BONE ANCHORING DEVICE WITH ENLARGED PIVOT ANGLE

CROSS-REFERENCE TO RELATED APPLICATION(S)

The present application claims priority to and the benefit of U.S. Provisional Patent Application Ser. No. 61/904,403, filed Nov. 14, 2013, the contents of which are hereby incorporated by reference in their entirety, and claims priority from European Patent Application EP 13 192 978.8, filed Nov. 14, 2013, the contents of which are hereby incorporated by reference in their entirety.

BACKGROUND

1. Field

The invention relates to a polyaxial bone anchoring device with an enlarged pivot angle. The bone anchoring device includes a bone anchoring element for anchoring in a bone or a vertebra, and a receiving part for coupling the bone anchoring element to a stabilization element such as a spinal rod, where the bone anchoring element is pivotable relative to the receiving part and can be pivoted away from a central axis with an enlarged pivot angle in at least one radial direction. The orientation of the enlarged pivot angle may be selectable within a range of 360° around the central axis. The bone anchoring element may be insertable into the receiving part from a bottom end of the receiving part.

2. Description of Related Art

A polyaxial bone anchoring device with an enlarged pivot angle that is selectable within a range of 360° around a central axis of the receiving part is known from US 2012/0136395 A1. This polyaxial bone anchoring device includes a sleeve-like insert piece that is positioned around a portion of the head of the bone anchoring element and that is configured to pivot in an accommodation space of the receiving part. The anchoring element and the insert piece can be locked at respective angles relative to the central axis of the receiving part. An enlarged pivot angle may be automatically achieved by pivoting the receiving part relative to the bone anchoring element in a specific direction. In one embodiment, the bone anchoring element may be inserted from the top end of the receiving part. In another embodiment, the bone anchoring element together with the sleeve-like insert piece may be inserted from the bottom end of the receiving part.

A polyaxial bone anchoring device of the bottom loading type are known, for example, from US 2010/0234902 A1.

SUMMARY

It is an object of the invention to provide a polyaxial bone anchoring device that permits pivoting of the bone anchoring element at an enlarged pivot angle in at least one direction and that provides a modular, robust design.

A polyaxial bone anchoring device according to embodiments of the invention is a bottom loading type bone anchoring device, where the anchoring element is insertable from the bottom end of the receiving part. A compressible cap member encompasses at least a portion of the head of the bone anchoring device. The cap member is seated in a sleeve-like insert piece that is solid, i.e. without slits or elastic portions. Consequently, the sleeve-like insert piece has a higher strength compared to a flexible sleeve of the same or similar dimensions. This renders the construct more robust, because high clamping forces can be exerted onto the cap member, that may be taken up by or transferred to the sleeve-like insert piece.

The cap member is sized such that the head is held therein by friction even if no pressure is exerted onto the cap member. When the receiving part is pivoted in order to align it for insertion of the rod, the angular position of the receiving part relative to the bone anchoring element is maintained and can be changed by overcoming the friction force. This permits convenient handling of the device during surgery.

At at least one side of its lower edge the cap member may have a recess or a cut portion that permits pivoting of the anchoring element at a larger angle in the direction where the recess or cut portion is located compared to the opposite direction or to another direction. An indication mark provided at the cap member may indicate the orientation of the enlarged pivot angle when the cap member is arranged in the receiving part and may cooperate with a tool that indicates the orientation to a user. The cap member is configured to rotate in the receiving part when no pressure is exerted onto it, so that the orientation of the enlarged pivot angle may be adjusted within a range of 360° around the central axis of the receiving part. The enlarged pivot angle may be greater than or equal to about 40° measured from the central axis of the receiving part.

A separate rod receiving element may be provided that is arranged in the receiving part on top of the cap member. The rod receiving element provides a seat for the rod and is configured to transmit pressure onto the cap member. It may be held by a first retaining element such that it cannot escape through the top end of the receiving part when the head is inserted into the cap member. Further, the rod receiving element may be held in a more downward position by a second retaining element such that the cap member is surrounded at least partially by the sleeve-like insert piece. In this position, the head of the bone anchoring element is in a pre-locking position wherein it is prevented from removal through the bottom end but not yet locked.

The rod receiving element may have side walls that extend above the surface of an inserted rod. This renders it suitable for use with a single part locking element that is configured to lock the head and the rod at the same time or sequentially, or for use with a two-part locking element that is configured to lock the head and the rod independently.

The receiving part, the sleeve-like insert piece, and the cap member may be pre-assembled, and the bone anchoring element can be inserted into the pre-assembled device from the bottom end of the receiving part in an easy manner. This permits insertion of the bone anchoring element into the bone first and mounting of the receiving part thereafter. By means of this design a modular system can be provided where the surgeon or any other personnel can select a suitable bone anchoring element such as a screw or a nail with a particular length and/or diameter, cannulated or non cannulated and various other features, and combine it with the pre-assembled receiving part. Lastly, the system permits selection of a suitable closure mechanism.

BRIEF DESCRIPTION OF THE DRAWINGS

Further features and advantages of the invention will become apparent from the description of embodiments by means of the accompanying drawings. In the drawings.

DETAILED DESCRIPTION

Figure 1:
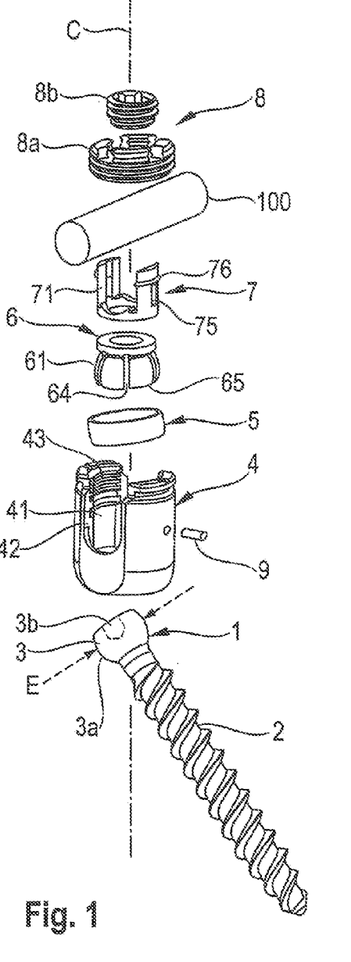
FIG. 1 shows a perspective exploded view of a polyaxial bone anchoring device with a spinal rod according to a first embodiment.
Figure 2:
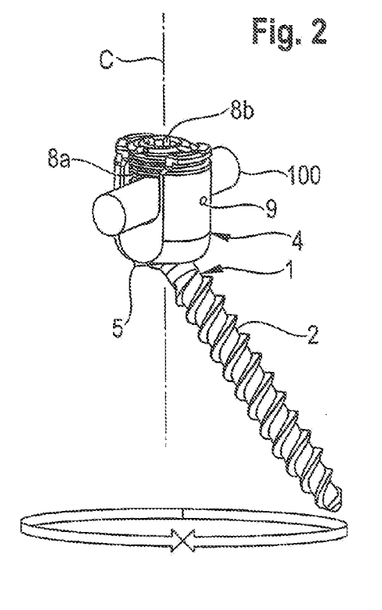
FIG. 2 shows a perspective view of the bone anchoring device of FIG. 1 in an assembled state.
Figure 3:
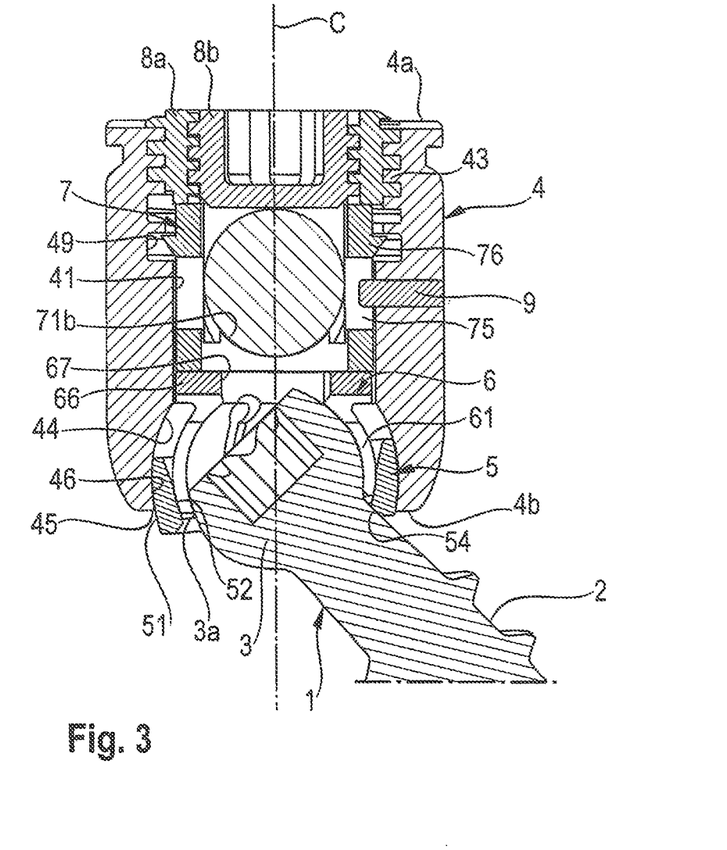
FIG. 3 shows a cross-sectional view of the bone anchoring device of FIGS. 1 and 2 in the assembled state with an inserted rod, the section being taken perpendicular to a rod axis.
Figure 4:
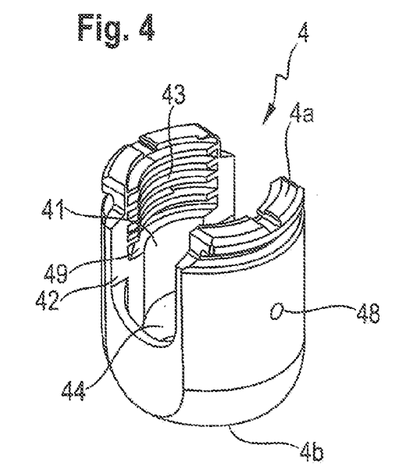
FIG. 4 shows a perspective view from a side of a receiving part of FIG. 1.
Figure 5:
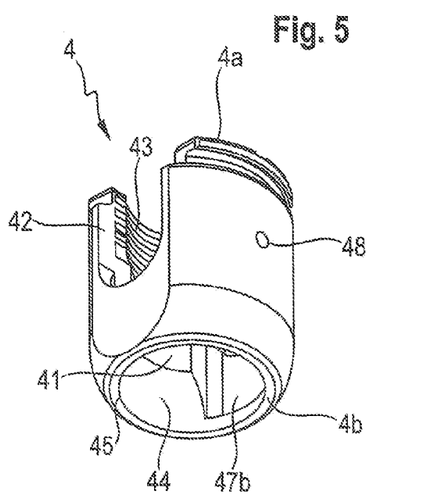
FIG. 5 shows a perspective view from the bottom of the receiving part of FIG. 4.
Figure 6:
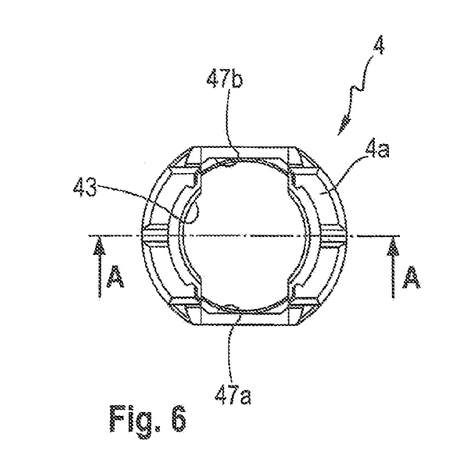
FIG. 6 shows a top view of the receiving part of FIGS. 4 and 5.
Figure 7:
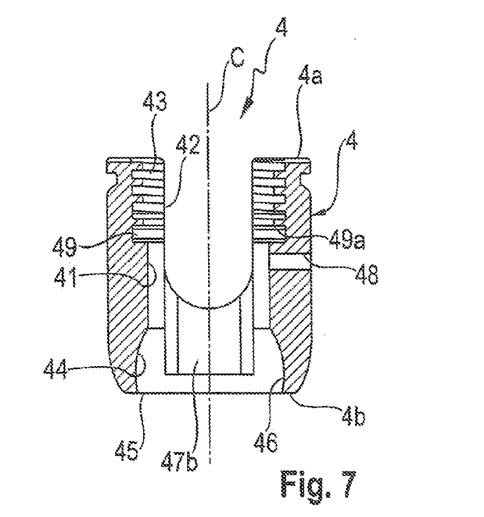
FIG. 7 shows a cross-sectional view of the receiving part of FIGS. 4 to 6, taken along line A-A in FIG. 6.
Figure 8:
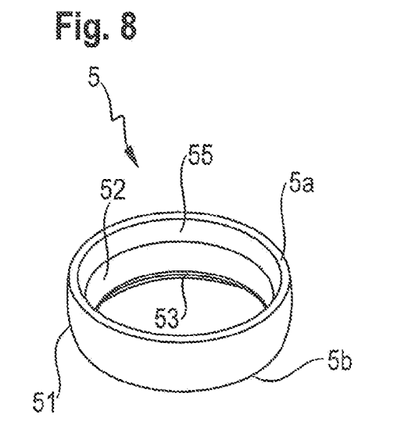
FIG. 8 shows a perspective view from the top of a sleeve-like insert piece of FIG. 1.
Figure 9:
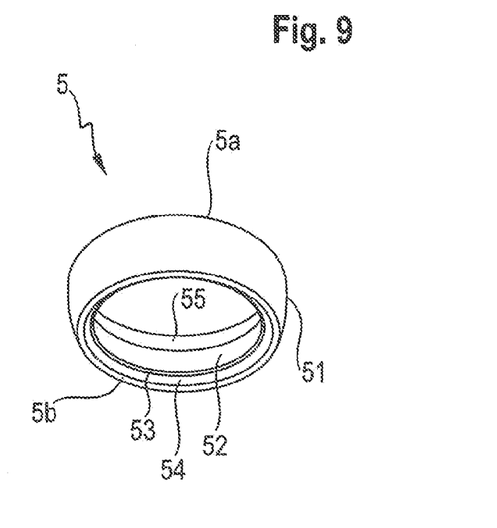
FIG. 9 shows a perspective view from the bottom of the sleeve-like insert piece of FIG. 8.
Figure 10:
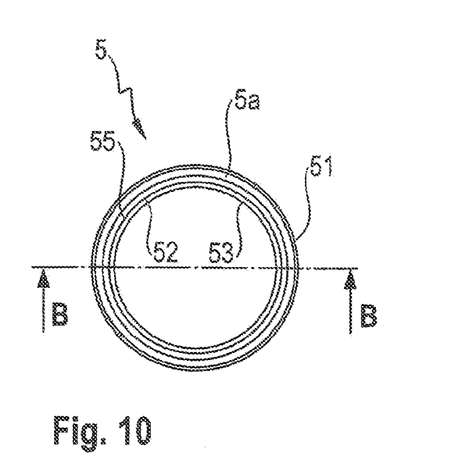
FIG. 10 shows a top view of the sleeve-like insert piece of FIGS. 8 and 9.
Figure 11:
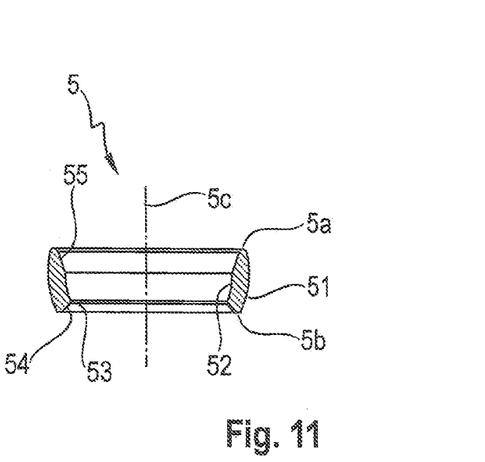
FIG. 11 shows a cross-sectional view of the sleeve-like insert piece of FIGS. 8 to 10, taken along line B-B in FIG. 10.
Figure 12:
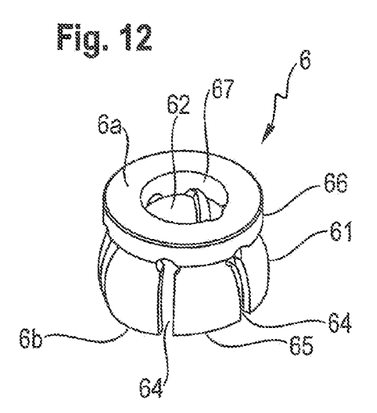
FIG. 12 shows a perspective view from the top of a cap member of FIG. 1.
Figure 13:
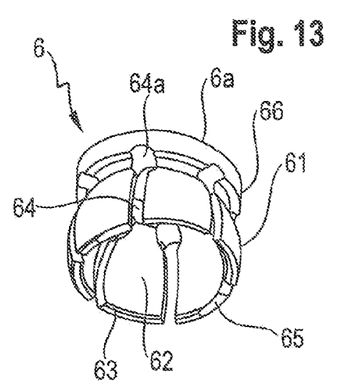
FIG. 13 shows a perspective view from the bottom of the cap member of FIG. 12.

As shown in FIGS. 1 to 3, a polyaxial bone anchoring device according to a first embodiment includes a bone anchoring element 1 in the form of a bone screw having a threaded shank 2 and a head 3. The head 3 typically has a spherical segment-shaped outer surface portion 3a and a recess 3b at its free end for engagement with a driver or tool. The spherical segment-shaped outer surface portion 3a of the head 3 includes a portion of the sphere with a greatest outer diameter E that forms a greatest diameter of the head 3. The head 3 may be held in a receiving part 4 that couples the bone anchoring element 1 to a stabilization rod 100. Positioned in the receiving part 4 are a sleeve-like insert piece 5 and a cap member 6 that is seated in the sleeve-like insert piece 5 and that exerts pressure onto the head 3. Furthermore, a separate rod receiving element 7 is provided for receiving the rod 100 and for transmitting pressure from the rod 100 onto the cap member 6. A locking device 8 comprising a first locking element 8a and a second locking element 8b is also provided for securing and fixing the rod 100 in the receiving part 4.

As depicted in further detail in FIGS. 3 to 7, the receiving part 4 has a first end which is a top end 4a and a second end which is a bottom end 4b as illustrated in FIGS. 3 to 7, a central axis C, and a passage 41 extending from the top end 4a in the direction of the bottom end 4b. Adjacent to the top end 4a, a substantially U-shaped recess 42 is provided that forms a channel for receiving the rod 100. By means of the recess 42, two free legs are formed which are provided with an internal thread 43 for cooperating with the first locking element 8a.

The passage 41, that may be coaxial with the central axis C, opens into an accommodation space 44 provided in a lower part of the receiving part 4 (e.g., nearer to the bottom end 4b). The accommodation space 44 has a lower opening 45 at the bottom end 4b of the receiving part 4. The accommodation space 44 further includes a seat portion 46 near the bottom end 4b of the receiving part 4 in which the sleeve-like insert piece 5 may be seated. The seat portion 46 has a spherical segment shape, in order to provide a socket for a ball-and-socket joint that is formed between the sleeve-like insert piece 5 and the receiving part 4. It should be noted that the seat portion 46 can also be tapered, or can have various other shapes that can be used to realize a ball-and-socket joint. An inner diameter of the lower opening 45 is smaller than an inner diameter of a middle portion of the accommodation space 44 (e.g., a portion of the accommodation space 44 with the greatest inner diameter). It shall also be noted that an inner diameter of the passage 41 does not need to be constant between the top end 4a and the accommodation space 44. The passage 41 may have different portions with different diameters.

In order to allow the sleeve-like insert piece 5 to be inserted from the top end 4a, two opposed recesses 47a, 47b are formed in the inner wall of the passage 41 and of the accommodation space 44. The recesses 47a, 47b are aligned with the U-shaped recess 42 and extend from a bottom of the U-shaped recess 42 into the accommodation space 44. The sizes of the recesses 47a, 47b are such that the sleeve-like insert piece 5 can be inserted from the top end 4a at a 90° angle tilted position. The widths of the recesses 47a, 47b are greater than a height of the sleeve-like insert piece 5 in its axial direction to facilitate insertion. The distance between the bottoms of the recesses 47a, 47b in a direction transverse to the central axis C is also greater than a maximum outer diameter of the sleeve-like insert piece 5. The recesses 47a, 47b extend into the accommodation space 44 to such an extent that tilting of the insert piece 5 into the seat portion 46 is possible.

Furthermore, the receiving part 4 has at least one pin hole 48 for receiving a pin 9 that forms a retaining element to retain or hold the respective pieces within the receiving part 4. The pin hole 48 may be arranged at a 90° angle relative to the channel axis of the U-shaped recess 42. Optionally, a second pin hole (not shown) may be provided on, for example, an opposite side of the receiving part 4.

At the end of the internal thread 43 that faces toward the bottom end 4b of the receiving part, an undercut portion 49 is provided, the upper edge 49a of which forms a stop for the rod receiving element 7 as described in further detail below. The undercut portion 49 forms two ring-segment shaped grooves with diameters that are larger than an inner diameter of the passage 41 between the internal thread 43 and the accommodation space 44.

The sleeve-like insert piece 5 is shown in more detail in FIGS. 8 to 11. The sleeve-like insert piece 5 has an upper edge 5a and a lower edge 5b. Between the upper edge 5a and the lower edge 5b, the sleeve-like insert piece may have a spherical segment-shaped outer surface portion 51. A largest outer diameter of the sleeve-like insert piece 5 is greater than the inner diameter of the lower opening 45 of the receiving part 4. Hence, the sleeve-like insert piece 5 cannot escape through the lower opening 45 when it is seated in the receiving part 4. The dimension or shape of the outer spherical surface portion 51 corresponds to that of the spherically-shaped seat portion 46 of the receiving part 4 in such a way that the sleeve-like insert piece 5 can pivot and rotate in the receiving part 4 when the insert piece 5 is seated in the seat portion 46. When the sleeve-like insert piece 5 rests in the seat portion 46, such that its central axis 5c is coaxial with the central axis C of the receiving part 4, the lower edge 5b projects out of the lower opening 45 of the receiving part 4. When the sleeve-like insert piece 5 is pivoted or angled in the receiving part 4, as shown, for example, in FIG. 3, at least a portion of the lower edge 5b still projects out of the lower opening 45.

The sleeve-like insert piece 5 is hollow and has a central portion 52 that is spherical segment-shaped and has a radius corresponding to a radius of a spherical segment-shaped outer surface portion of the cap member 6, which is described in greater detail below. A lower end of the central portion 52 forms a shoulder 53. An inner diameter of the shoulder 53 is smaller than a largest outer diameter of the spherical segment-shaped portion of the cap member 6 when the head 3 is inserted into the cap member 6, so that the cap member 6 with the inserted head 3 can rotate and pivot in the spherical central portion 52 of the sleeve-like insert piece 5, similar to a ball-and-socket joint, and the head 3 cannot be removed through the bottom end 4b of the receiving part 4 when the spherical surfaces of the sleeve-like insert piece 5 and the cap member 6 are engaged. Between the shoulder 53 and the lower edge 5b, a tapered portion 54 is provided that widens in the direction of the lower edge 5b to better facilitate angulation of the bone anchoring element 1 until the shank 2 comes into contact with the lower edge 5b. Between the spherical central portion 52 and the upper edge 5a, a tapered portion 55 is provided which widens in the direction of the upper edge 5a. An inner diameter of the tapered portion 55 and of a transition between the tapered portion 55 and the spherical portion 52 are greater than a largest outer diameter of the flexible portion of the cap member 6 with the inserted head 3, so that the cap member 6 with the inserted head 3 can move from the upper edge 5a into the spherical central portion 52 of the sleeve-like insert piece 5.

Spherical center points of the spherical central portion 52 and of the outer spherical portion 51 may overlap in an axial direction. However, in some embodiments, the center point of the spherical central portion 52 may instead be shifted toward the lower edge 5b relative to the center point of the outer spherical portion 51. This may further increase the range of angulation of the bone anchoring element 1. A height of the sleeve-like insert piece 5 in an axial direction is less than a height of the head 3 in an axial direction, such that when the head 3 is inserted into the cap member 6 and the cap member 6 is inserted into the sleeve-like insert piece 5, as shown for example in FIG. 3 and in FIG. 25, a portion of the spherical outer surface portion 3a of the head 3 may still project from the upper edge 5a of the sleeve-like insert piece 5.

The cap member 6 will be described with reference to FIGS. 1 to 3 and 12 to 15. The cap member 6 is a pressure member that is configured to clamp the head 3 upon compression of a portion of the cap member 6. Cap member 6 comprises a first or upper end 6a and an opposite second or lower end 6b, and a central axis 6c extends through the upper end 6a and the lower end 6b. When the cap member 6 is inserted into the receiving part 4, the central axis 6c of the cap member is coaxial with the central axis C of the receiving part 4.

Adjacent to the lower end 6b, the cap member 6 comprises a first portion 61 that is flexible in such a way that it can be compressed and expanded in a radial direction. The first portion 61 has a hollow interior chamber 62 that is substantially spherical segment-shaped to clamp the head 3 therein. At the lower end 6b, an opening 63 is provided for inserting the head 3 into the hollow interior chamber 62. The outer surface of the first portion 61 comprises a spherical segment-shaped portion that is configured to cooperate with the spherical segment-shaped central portion 52 of the sleeve-like insert piece 5. The shape of the first portion 61 resembles that of a cap that is to be placed on the head 3. A plurality of slits 64 extend from the lower end 6b through the first portion 61 in a direction toward the upper end 6a. The slits 64 are open toward the lower end 6b and closed at the opposite end where they may each have an enlarged area 64a to facilitate compression or expansion of the first portion 61. The enlarged area 64a may have a circular shape. The number and dimensions of the slits 64 are such that the walls of the first portion 61 are flexible enough to snap onto the head 3 when the head 3 is inserted through the opening 63.

The size of the first portion 61 in the axial direction is such that when the head 3 is inserted fully into the cap member 6, the lower end 6b of the cap member 6 extends beyond a portion of the head 3 that includes the largest outer diameter E of the head 3 in the direction toward the shank 2. A maximum outer diameter of the first portion 61 of the cap member 6 in the neutral position, i.e., when the first portion 61 is neither compressed nor expanded, is smaller than an inner diameter of the accommodation space 44 of the receiving part 4 and also smaller than an inner diameter of the upper tapered portion 55 of the sleeve-like insert piece 5. Therefore, it is possible to insert the head 3 through the opening 63 into the cap member 6 when the cap member 6 is placed in the receiving part 4 and the first portion 61 extends into the accommodation space 44 and partially into the sleeve-like insert piece 5.

The dimension of the cap member 6 relative to the head 3 is such that when the head 3 is inserted through the lower opening 63 into the hollow interior chamber 62 of the cap member 6, it is held therein by friction. This means that an angular position of the bone anchoring element 1 relative to the cap member 6 can be adjusted by applying a force that overcomes the friction force.

The lower opening 63 of the cap member 6 further has a bounding edge that has a portion that is configured to allow the head 3 to pivot at a greater angle in one direction compared to other directions. For example, the cap member 6 may have a slanted lower edge portion 65 at its lower end 6b where the cap member 6 is shorter in an axial direction over a particular range of angles around the central axis 6c compared to the other portions of the cap member 6. The slanted edge portion 65 may be achieved by cutting away a portion of the cap member 6 in an inclined cut. By means of the slanted lower edge portion 65, the bone anchoring element can abut with its shank 2 against the lower edge 6b of the cap member at a larger angle in the direction of the slanted lower edge portion 65 as compared to other directions. An enlarged pivot angle can be achieved by other means also, for example, instead of the slanted lower edge portion 65, a recess can be provided that allows the shank 2 to extend more outwardly or be pivoted at a greater angle, as compared to other directions.

The cap member 6 further comprises, adjacent to the flexible first portion 61, a non-flexible second portion 66 that has a substantially cylindrical outer shape with an outer diameter that is only slightly smaller than an inner diameter of the passage 41 in the receiving part 4, so that the second portion 66 can move in the passage 41. Due to the cylindrical shape, the second portion 66 is also rotatable in the receiving part 4. The cap member 6 additionally comprises a coaxial bore 67 that extends from the upper end 6a into the hollow interior chamber 62. As can be seen in particular in FIG. 14, by means of the coaxial recess 67 a ring-shaped flat upper surface is formed at the upper end 6a. This surface serves for cooperating with a lower surface of the rod receiving element 7, to be described in greater detail below.

Figure 14:
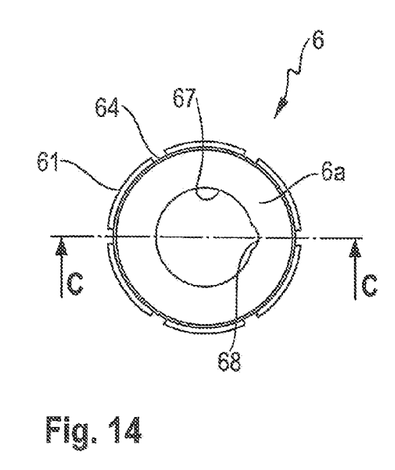
FIG. 14 shows a top view of the cap member of FIGS. 12 and 13.
Figure 15:
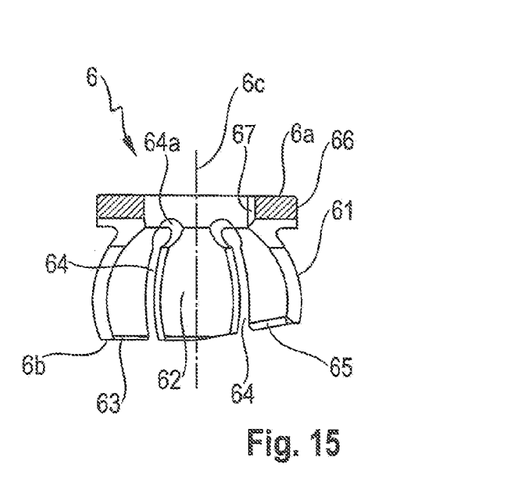
FIG. 15 shows a cross-sectional view of the cap member of FIGS. 12 to 14, taken along line C-C in FIG. 14.
Figure 16:
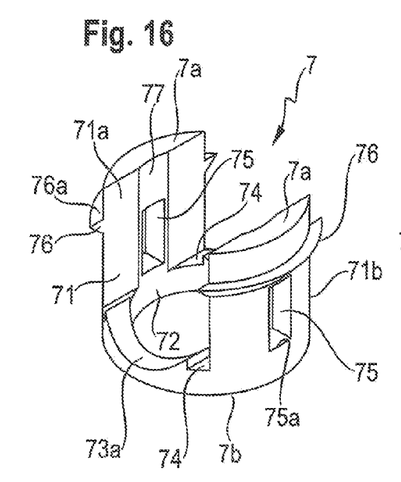
FIG. 16 shows a perspective view from the side of a rod receiving element of FIG. 1.
Figure 17:
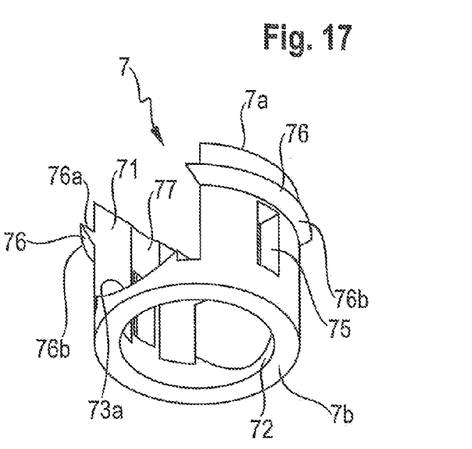
FIG. 17 shows a perspective view from the bottom of the rod receiving element of FIG. 16.
Figure 18:
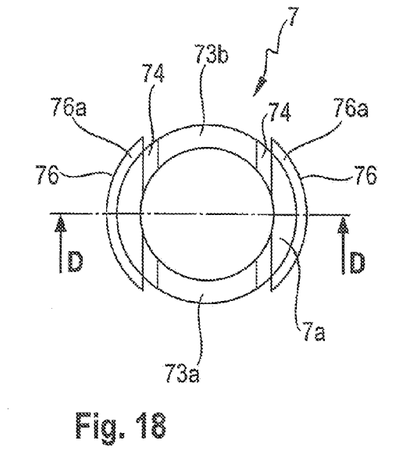
FIG. 18 shows a top view of the rod receiving element of FIGS. 16 and 17.
Figure 19:
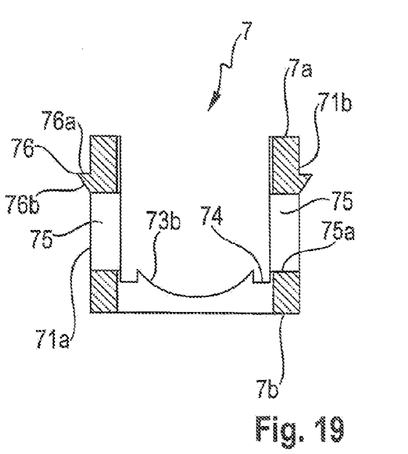
FIG. 19 shows a cross-sectional view of the rod receiving element of FIGS. 16 to 18, taken along line D-D in FIG. 18.

In the inner wall forming the coaxial bore 67, a single recess 68 is formed that serves as an indication mark for indicating the position of the slanted lower edge portion 65 that provides the enlarged pivot angle. The recess 68 is aligned with the slanted lower edge portion 65 in a circumferential direction so that, even if the position of the slanted lower edge portion 65 cannot be seen from above, the recess 68 indicates the position of the slanted lower edge portion 65. The recess 68 may cooperate with a corresponding tool that engages the cap member 6, for example through the coaxial bore 67 and that has a corresponding indication mark, such as a projection, for example, that indicates a specific circumferential orientation or position around the central axis 6c. Hence, by rotating the cap member 6, for example, with such a tool, the orientation of the enlarged pivot angle can be adjusted to a desired orientation relative to the receiving part 4.

Referring now to FIGS. 1 and 16 to 19, the rod receiving element 7 is a part that is separate from the cap member 6. Rod receiving element 7 is a substantially cylindrical part that comprises a first or upper end 7a with a free end surface and an opposite second or lower end 7b with a free end surface. Adjacent to the first end 7a there is a substantially rectangular recess 71 that cuts out a portion of the cylinder such that two free upstanding legs 71a, 71b remain. Adjacent to the lower end 7b there is an opening 72, preferably a circular opening, that extends through the rod receiving element 7 into the recess 71. An inner diameter of the opening 72 is greater than the inner diameter of the coaxial bore 67 of the cap member 6 so that the end surface of the lower end 7b is configured to fully contact the upper end surface of the upper end 6a of the cap member 6 when in the receiving part 4.

On the bottom of the recess 71 between the legs 71a and 71b, two concave cylinder-segment shaped rod supporting projections 73a, 73b are provided on respective sides of the opening 72. The radius of each of the concave portions of the rod supporting projections 73a, 73b is preferably selected such that it is adapted to the radius of the specific rod to be used. The rod supporting projections 73a, 73b may be separated from the legs 71a, 71b by a groove 74 on either side of each projection. The width of the recess 71 is such that the rod 100 can be received in the recess 71. When the rod 100 is inserted into the recess 71 of the rod receiving element 7, the rod 100 can rest on the rod supporting projections 73a, 73b. A height of the legs 71, 71b is such that the upper end 7a is located above the upper rod surface of the rod 100 when the rod 100 is placed into the channel formed by the recess 71 and rests on the rod supporting projections 73a, 73b, as shown in FIG. 3.

An outer diameter of the rod receiving element 7 is only slightly smaller than an inner diameter of the passage 41 of the receiving part 4, so that the rod receiving element 7 can move in the passage 41 to some extent and can be guided therein.

The rod receiving element 7 further comprises at each leg 71a, 71b an elongate recess 75 that extends substantially from the bottom of the recess 71 to a distance from the first end 7a. The recesses 75 extend completely through each leg 71a, 71b in a radial direction. The recesses 75 have such a width that the pin 9 can be accommodated therein. A bottom end 75a of each elongate recess 75 forms a stop for the pin 9 when the pin 9 extends into the recess 75. The abutment of the pin 9 against the stop prevents the rod receiving element 7 from escaping through the first end 4a of the receiving part 4 when the cap member 6 is in an insertion position. Furthermore, the corresponding recess 75 may serve with the pin 9 as a securing device to maintain the alignment between the recess 42 of the receiving part 4 and the channel formed by the recess 71 of the rod receiving element 7. The pin 9 forms a first retaining element or feature that secures the receiving part 4 pre-assembled with the sleeve-like insert piece 5, the cap member 6 and the rod receiving element 7 against loss of the rod receiving element 7 and/or the cap member 6. Providing two recesses 75, one on each side, permits insertion of the rod receiving element 7 into the receiving part 4 in two orientations that are offset by 180°. This is more convenient, for example, if only one pin 9 is used.

In addition, the rod receiving element 7 has on each leg 71a, 71b, at a position above the recesses 75, a circumferentially extending projection 76 with a flat upper surface 76a and an inclined lower surface 76b. A maximum outer diameter of the projections 76 is slightly larger than an inner diameter of the internal thread 43 of the receiving part 4. When the rod receiving element 7 is inserted into the passage 41, the legs 71a, 71b are slightly compressed, so that the rod receiving element 7 can be moved downward, which is possible or more easily accomplished due to the inclination of the lower side 76b of the projection 76. As explained in further detail below, the projection 76 is configured to enter into the undercut portion 49, and the upper edge 49a of the undercut portion 49 forms a second retaining element or feature that cooperates with the flat upper surface 76a of the projection 76 to prevent upward movement of the rod receiving element 7.

Furthermore, on each leg 71a, 71b, a longitudinally extending cylinder segment-shaped recess 77 is provided that extends from the bottom of the recess 71 to the first end 7a.

The bone anchoring device, as a whole or in part, is made of a bio-compatible material, such as a bio-compatible metal or a metal alloy, for example titanium, stainless steel, of a nickel-titanium alloy, for example, Nitinol, or of a bio-compatible plastic material, such as, for example, a material from the group of polyaryletherketones, such as polyetheretherketone (PEEK).

Figure 20:
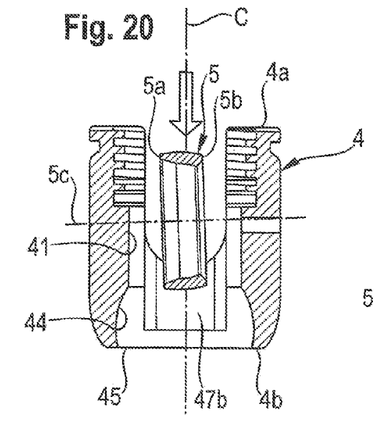
FIG. 20 shows a cross-sectional view of a first step of assembling the receiving part and the sleeve-like insert piece of the polyaxial bone anchoring device according to the first embodiment, the section being taken perpendicular to a rod axis.
Figure 21:
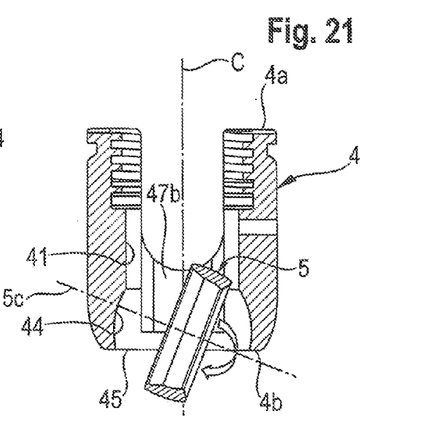
FIG. 21 shows a cross-sectional view of a second step of assembling the receiving part and the sleeve-like insert piece of the polyaxial bone anchoring device according to the first embodiment.
Figure 22:
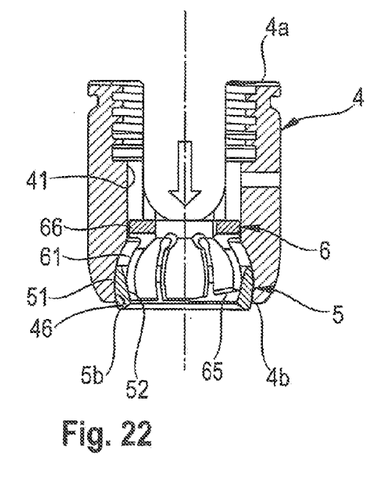
FIG. 22 shows a cross-sectional view of a third step of assembling the polyaxial bone anchoring device, wherein the cap member is inserted.
Figure 23:
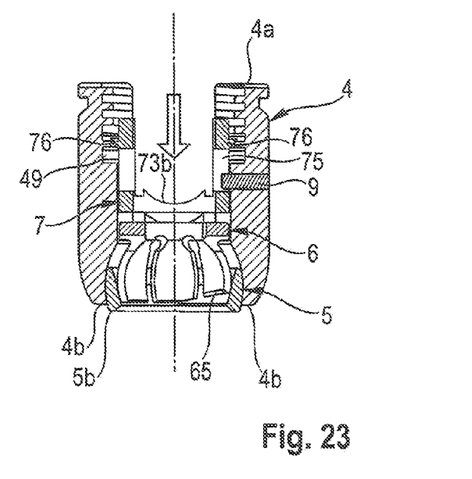
FIG. 23 shows a cross-sectional view of a fourth step of assembling the polyaxial bone anchoring device, wherein the rod receiving element is inserted.

Referring now to FIGS. 20 to 23, the receiving part 4 may be pre-assembled with the sleeve-like insert piece 5 and the cap member 6 as well as the rod receiving element 7 in the following manner. First, as shown in FIG. 20, the sleeve-like insert piece 5 is inserted from the top end 4a into the receiving part 4 in a tilted orientation, i.e., the central axis 5c of the sleeve 5 is perpendicular to the central axis C of the receiving part 4. The sleeve-like insert piece 5 is inserted in such an orientation that it extends into the recesses 47a, 47b of the receiving part 4. Next, as shown in FIG. 21, when the sleeve-like insert piece 5 extends at least partially through the lower opening 45 of the receiving part 4, the insert piece 5 is tilted such that it can assume in the accommodation space 44 an orientation where the central axis 5c of the insert piece 5 is coaxial with the central axis C of the receiving part 4, as further depicted in FIG. 22. Then, the cap member 6 is inserted from the top end 4a into the receiving part until the lower part of the first portion 61 is held in the spherical central portion 52 of the sleeve-like insert piece 5, as also depicted in FIG. 22. In the next step, as shown in FIG. 23, the rod receiving element 7 is inserted from the upper end 4a into the passage 41, such that the recess 71 for receiving the rod 100 is aligned with the recess 42 of the receiving part 4. Subsequently, the pin 9 is inserted into the pin hole 48 until the pin 9 engages the elongate recess 75 at one of the legs 71b of the rod receiving element 7. By means of this, the rotational position of the rod receiving element 7 is secured in the receiving part 4, and the rod receiving element 7 is secured against escaping through the top end 4a of the receiving part 4.

The orientation in which the enlarged pivot angle is provided can be adjusted by rotating the cap member 6 once it has been inserted into the receiving part 4, or after inserting the head 3 into the cap member 6 thereafter.

Figure 24:
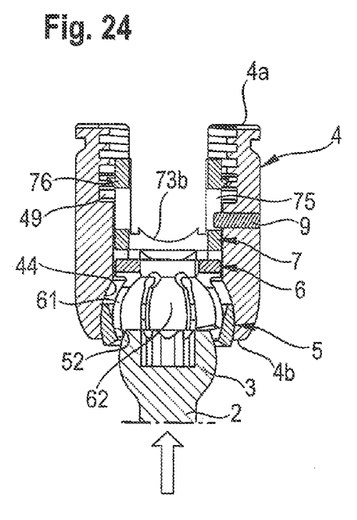
FIG. 24 shows a cross-sectional view of a first step of inserting the bone anchoring element into the receiving part that is pre-assembled with the sleeve-like insert piece, the cap member, and the rod receiving element.

The circumferential projection 76 on each of the legs 71a, 71b of the rod receiving element 7 is in a position above the undercut 49 when the cap member 6 is in an insertion position for the head 3, as shown in FIGS. 23 and 24.

Figure 25:
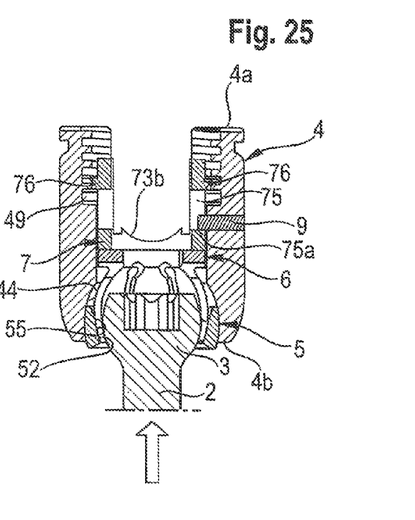
FIG. 25 shows a second step of inserting the bone anchoring element into the receiving part.
Figure 26:
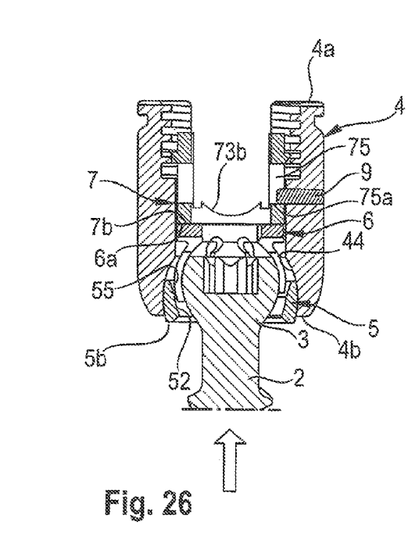
FIG. 26 shows a cross-sectional view of a third step of inserting the bone anchoring element into the receiving part.

In the next step, the bone anchoring element 1 is connected to the receiving part 4. Either the bone anchoring element 1 has been already inserted into a bone part or a vertebra and the receiving part 4 is mounted onto the head 3 of the bone anchoring element 1 in situ at the operation site, or the bone anchoring element 1 is connected beforehand to the receiving part 4 and thereafter inserted into the bone or vertebra. As shown in FIGS. 24 and 25, the head 3 is inserted through the sleeve-like insert piece 5 into the interior chamber 62 of the cap member 6. Thereby, the cap member 6 is moved upward toward the upper end 4a of the receiving part 4 until it abuts with its upper end 6a against the lower end 7b of the rod receiving element 7. This moves the rod receiving element 7 slightly upward until the bottom 75a of the elongate recess 75 abuts against the pin 9. The projection 76 extends into the space between the crests of the inner thread 43 of the receiving part 4 and is thus allowed to move in an axial direction in that space. When the head 3 enters the hollow interior chamber 62, the first portion 61 of the cap member 6 expands within the upper tapered portion 55 of the sleeve-like insert piece 5 until the head 3 has fully entered the interior chamber 62, as depicted in FIG. 26.

Figure 27:
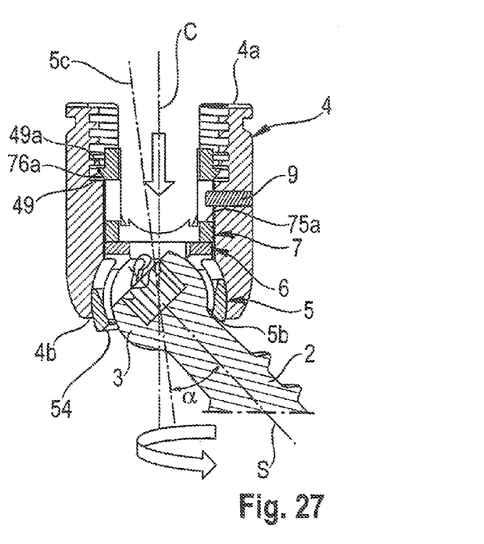
FIG. 27 shows a cross-sectional view of the receiving part pre-assembled with the sleeve-like insert piece, the cap member, and the rod receiving element, and with the inserted head of the bone anchoring element in a pre-locking condition.
Figure 28:
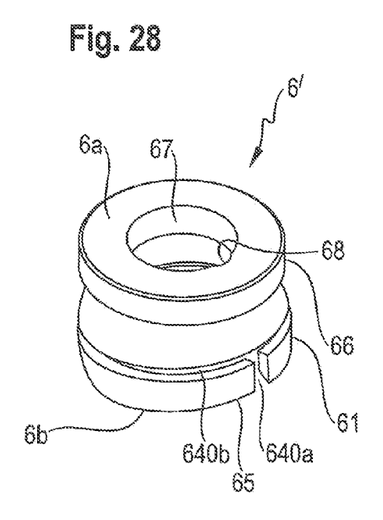
FIG. 28 shows a perspective view from a side of a cap member of the polyaxial bone anchoring device according to a second embodiment.
Figure 29:
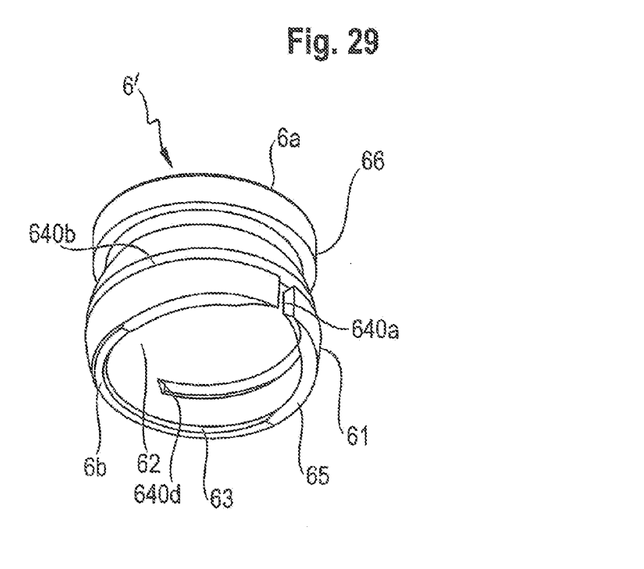
FIG. 29 shows a perspective view from the bottom of the cap member of FIG. 28.
Figure 30:
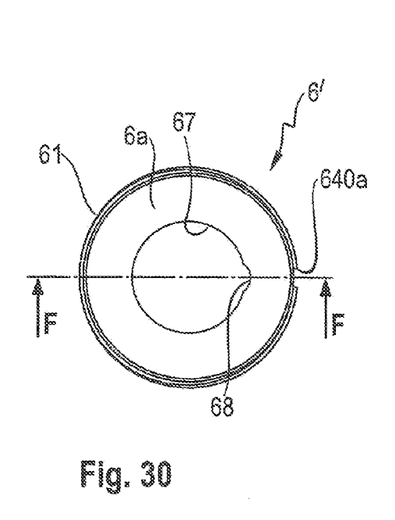
FIG. 30 shows a top view of the cap member of FIGS. 28 and 29.
Figure 31:
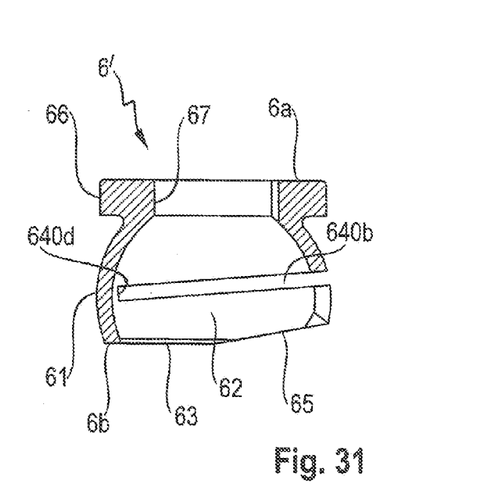
FIG. 31 shows a cross-sectional view of the cap member of FIGS. 28 to 30, taken along line F-F in FIG. 30.

In a next step as shown in FIG. 27, the rod receiving element 7 is moved downward and shifts the cap member 6 with the inserted head 3 into the spherical central portion 52 of the sleeve-like insert piece 5. The rod receiving element 7 is pressed downward until the upper surface 76a of the projection 76 snaps into the undercut 49. In this position, the upper edge 49a of the undercut 49 retains the rod receiving element 7, so that the rod receiving element 7 cannot move upward again. Simultaneously, the first portion 61 of the cap member 6 is compressed by the sleeve-like insert piece 5 to such an extent that the lower opening 63 of the cap member 6 is narrowed, so that the head 3 can no longer be removed from the receiving part 4. This is the pre-locking position of the cap member 6. Because the head 3 is held by friction within the first portion 61 of the cap member 6 due to the dimensions of the cap member 6 relative to the head 3, the angular position of the bone anchoring element 1 relative to the receiving part 4 is maintained in a preliminary manner, but can still be manually or otherwise pivoted or adjusted.

In the pre-locking position of the cap member 6, the head 3 is pivotable relative to the receiving part 4 in all directions. When the head 3 pivots with respect to the receiving part 4, the shank 2 of the bone anchoring element 1 can abut against the lower tapered portion 54 of the sleeve-like insert piece 5. Thereby, the sleeve-like insert piece 5 can pivot in the seat portion 46 of the accommodation space 44 of the receiving part 4 as shown in FIG. 27. The bone anchoring element 1 can pivot to the side of the cap member 6 with the slanted lower edge portion 65 at a greater angle than in other directions. The enlarged pivot angle $\alpha$, defined as the maximum angle that the shank axis S can pivot from the central axis 5c of the insert piece 5, may be equal to or greater than 40° measured from the central axis 5c. When the head 3 pivots in the cap member 6, a portion of the head 3 may extend into the coaxial bore 67 of the cap member 6.

Finally, the rod 100 is inserted into the receiving part 4 and the rod receiving element 7, and the locking device 8 is inserted into the receiving part 4. For a two-part locking device 8, as shown in FIG. 1, the first locking element 8a acts on the upper end 7a of the legs 71a, 71b of the rod receiving element 7. If the first locking element 8a is tightened, pressure is transmitted through the rod receiving element 7 and the cap member 6 onto the head 3 and the sleeve-like insert piece 5. By means of the first locking element 8a being tightened, the sleeve-like insert piece 5 is pressed into the seat 46 of the accommodation space 44. When the first locking element 8a is finally tightened, the relative positions of the head 3 in the cap member 6 and the sleeve-like insert piece 5 in the accommodation space 44 are both locked, so that the position of the bone anchoring element 1 relative to the receiving part 4 is fixed. Tightening of the second locking element 8b then fixes the rod 100. With the solid, non-elastic sleeve-like insert piece 5, the construct of the device is more robust and can withstand higher locking forces compared to a device with a flexible sleeve.

In an alternate embodiment, instead of the two-part locking device 8, a single part locking device (not shown) can be used that may include, for example, a set screw with a central projection that acts on the rod only. The pressure exerted by the single part locking device is transferred to the rod 100 onto the rod receiving element 7 and the cap member 6. The rod 100 and the head 3 can be fixed simultaneously in this embodiment. Other kinds of locking devices may be contemplated, for example, a sequential locking device that comprises a single drive portion only and that fixes the head and the rod sequentially.

In clinical use, at least two bone anchoring elements are anchored in a bone or in two vertebrae and are connected by a rod. In one embodiment, the surgeon or any other personnel can select a desired bone anchoring element and combine it with the receiving part pre-assembled with the sleeve-like insert piece, the cap member and the rod receiving element. The design of the bone anchoring device allows the selection of an appropriate bone anchoring element in terms of diameter, length, and other features. Furthermore, a suitable locking device may be selected. Hence, a modular system is provided which includes various elements which can be individually chosen and adapted to a particular application.

A further embodiment of the cap member will be described with reference to FIGS. 28 to 31. The cap member 6' differs from the cap member 6 in the design of the slits. Instead of a plurality of longitudinal slits, one or more substantially horizontally extending slits are provided. The cap member 6' has a first substantially vertical slit 640a that extends from the lower edge 6b and opens into a substantially horizontal slit 640b that extends around the portion 61 in a slightly slanted manner from a first end (not shown) at one side to a second end 640d at a second side. The substantially vertical slit 640a may be preferably at the side where the slanted lower edge 65 is provided. All other parts of the cap member 6' are the same as or similar to the cap member 6 and have the same reference numerals, and the descriptions thereof will not be repeated. The receiving part 4 and the rod receiving element 7 may also be the same as or similar to those of the first embodiment. With the cap member 6' according to the second embodiment, an insertion force for inserting the head into the cap member 6' may be reduced compared to the cap member 6 of the first embodiment, while the holding force in the pre-locking position may be the same or similar for both cap members.

Various other modifications of the embodiments described above may also be contemplated. For example, the receiving part is not limited to the exact shape shown. The recess 42 does not have to have an exact U-shape. The retaining elements can be realized in other ways, for example, through spring portions, snap rings, or other constructs that prevent movement of the rod receiving element and the receiving part relative to each other.

The head 3 and correspondingly the interior chamber 62 of the cap member 6 can also have other shapes. For example, two opposite flattened portions may be present that render the pivot connection between the parts monoplanar.

Various different kinds of anchoring elements can also be used and combined with the receiving part. These anchoring elements may be, for example, screws with different lengths, screws with different diameters, cannulated screws, screws with different thread forms, nails, hooks, etc. For some anchoring elements, the head and the shaft may also be separate parts that are connectable to each other.

All different kinds of rods can also be used. While rods with a smooth surface are shown, roughened rods or rods having other structures may be used. The rods may also be flexible rods.

While a number of different embodiments are disclosed herein, it should be appreciated and understood that different components from the different embodiments can be mixed and matched to produce a variety of still other different embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
   a receiving part configured to be pivotably connected to a head of an anchoring element, the receiving part having a first end, a second end, a central axis extending through the first end and the second end, a channel intersecting the central axis for receiving a rod, an accommodation space for accommodating the head, the accommodation space having an opening at the second end, and a passage extending along the central axis from the first end to the accommodation space;
   a cap member having a first portion configured to be positioned in the accommodation space and to hold the head, wherein the first portion is expandable in the accommodation space to allow insertion of the head and compressible to exert pressure on the head; and
   a non-expandable sleeve-like insert piece comprising a spherical segment-shaped and continuous outer surface portion that forms an endless ring, wherein the insert piece is configured to be positioned at least partially around the first portion of the cap member;
   wherein when the cap member and the insert piece are in the receiving part and the insert piece is positioned at least partially around the first portion of the cap member, the insert piece is pivotable relative to the cap member, such that an angle formed between a central axis of the insert piece and a central axis of the cap member is adjustable.

2. The polyaxial bone anchoring device of claim 1, wherein the first portion of the cap member has a hollow interior space for accommodating the head and an opening for inserting the head, and wherein the opening of the cap member has a bounding edge having an asymmetry relative to the central axis to permit the head to pivot at a greater angle in one direction relative to the central axis compared to other directions relative to the central axis.

3. The polyaxial bone anchoring device of claim 2, wherein the cap member comprises an indication mark configured to indicate an orientation of the asymmetry of the bounding edge when the cap member is in the receiving part.

4. The polyaxial bone anchoring device of claim 1, wherein the cap member is rotatable in the receiving part when the first portion is not compressed.

5. The polyaxial bone anchoring device of claim 1, wherein the cap member comprises a second portion having a substantially flat, ring-shaped surface configured to face the first end of the receiving part when the cap member is in the receiving part.

6. The polyaxial bone anchoring device of claim 1, wherein when the insert piece is seated in the receiving part and a central axis of the insert piece is coaxial with the central axis of the receiving part, a lower edge of the insert piece extends out of the opening of the accommodation space in a direction away from the receiving part.

7. The polyaxial bone anchoring device of claim 1, wherein the insert piece has a spherical segment-shaped inner surface configured to cooperate with a spherical segment-shaped outer surface of the first portion of the cap member, such that the insert piece can pivot with respect to the cap member.

8. The polyaxial bone anchoring device of claim 1, wherein the insert piece is pivotable with respect to the central axis of the receiving part and wherein the insert piece is configured to be locked at an angle relative to the central axis of the receiving part by exerting pressure with the cap member onto the insert piece.

9. The polyaxial bone anchoring device of claim 1, further comprising a rod receiving portion configured to be positioned in the passage of the receiving part between the cap member and the first end of the receiving part.

10. The polyaxial bone anchoring element of claim 9, wherein the rod receiving portion is configured to transmit a pressure force onto the first portion of the cap member.

11. The polyaxial bone anchoring device of claim 9, wherein a retaining element is configured to act on the rod receiving portion to prevent the rod receiving portion from escaping through the first end of the receiving part.

12. The polyaxial bone anchoring device of claim 9, wherein a retaining element is configured to act on the rod receiving portion to hold the first portion of the cap member and the insert piece in respective positions in the receiving part such that expansion of the first portion of the cap member is restricted and removal of the head from the cap member is prevented.

13. The polyaxial bone anchoring device of claim 9, wherein the rod receiving portion has a channel for receiving the rod, the channel being defined by sidewalls configured to extend closer to the first end of the receiving part than an upper surface of an inserted rod.

14. The polyaxial bone anchoring device of claim 9, wherein the rod receiving portion is separate from the cap member and comprises a lower surface portion configured to face an upper surface portion of the cap member and to cooperate with the upper surface portion of the cap member to transmit pressure onto the cap member.

15. The polyaxial bone anchoring device of claim 11, wherein the rod receiving portion comprises a channel for receiving the rod, and wherein the retaining element is configured to align the channel of the rod receiving portion and the channel of the receiving part.

16. A polyaxial bone anchoring device comprising:
an anchoring element comprising a shank for anchoring in bone and a head;
a receiving part configured to be pivotably connected to the head of the anchoring element, the receiving part having a first end, a second end, a central axis extending through the first end and the second end, a channel intersecting the central axis for receiving a rod, an accommodation space for accommodating the head, the accommodation space having an opening at the second end, and a passage extending along the central axis from the first end to the accommodation space;
a cap member having a first portion configured to be positioned in the accommodation space and to hold the head, wherein the first portion is expandable in the accommodation space to allow insertion of the head and compressible to exert pressure on the head; and
a non-expandable sleeve-like insert piece comprising a spherical segment-shaped outer surface portion, wherein the insert piece is configured to be positioned at least partially around the first portion of the cap member;
wherein when the head, the cap member, and the insert piece are in the receiving part with the cap member holding the head and the insert piece positioned at least partially around the first portion of the cap member, the head is pivotable relative to the cap member, such that an angle formed between a central axis of the anchoring element and a central axis of the cap member is adjustable.

17. The polyaxial bone anchoring device of claim 16, wherein the first portion of the cap member has a hollow interior space with a spherical segment-shaped inner wall for accommodating the head of the anchoring element and an opening for inserting the head, and wherein the opening of the cap member has a bounding edge configured to allow the head to pivot at a greater angle in one direction relative to the central axis compared to other directions relative to the central axis.

18. The polyaxial bone anchoring device of claim 16, wherein the cap member is configured to hold the head of the anchoring element by friction when the head is inserted in the cap member.

19. The polyaxial bone anchoring device of claim 16, wherein the insert piece has an opening with a diameter that is greater than or equal to a maximum diameter of the first portion of the cap member when the head is inserted in the cap member.

20. The polyaxial bone anchoring device of claim 16, wherein when the cap member and the insert piece are in the receiving part and the head of the anchoring element is inserted in the cap member, the receiving part, the insert piece, and the anchoring element are also pivotable relative to one another, and wherein the anchoring element and the insert piece are configured to be locked at respective angles relative to the central axis of the receiving part by exerting pressure with the cap member on the head and the insert piece.

21. A method of coupling a rod to a bone via a polyaxial bone anchoring device, the bone anchoring device comprising an anchoring element having a shank for anchoring in the bone and a head, a receiving part configured to be pivotably connected to the head, the receiving part having a first end, a second end, a central axis extending through the first end and the second end, a channel intersecting the central axis for receiving a rod, an accommodation space for accommodating the head, the accommodation space having an opening at the second end, and a passage extending along the central axis from the first end to the accommodation space, a cap member having a first portion configured to be positioned in the accommodation space and to hold the head, wherein the first portion is expandable in the accommodation space to allow insertion of the head and compressible to exert pressure on the head, a non-expandable sleeve-like insert piece comprising a spherical segment-shaped outer surface portion, wherein the insert piece is configured to be positioned at least partially around the first portion of the cap member, wherein when the head, the cap member, and the insert piece are in the receiving part with the cap member holding the head and the insert piece positioned at least partially around the first portion of the cap member, the head is pivotable relative to the cap member, such that an angle formed between a central axis of the anchoring element and a central axis of the cap member is adjustable, and a locking device, the method comprising:
- inserting the shank of the bone anchoring element into a bone;
- adjusting an angular position of the receiving part relative to the anchoring element;
- inserting the rod into the channel of the receiving part;
- advancing the locking device in the channel of the receiving part to lock the angular position of the receiving part relative to the anchoring element and to lock the rod in the channel of the receiving part.

22. The method of claim 21, further comprising inserting the head of the anchoring element through the opening of the accommodation space of the receiving part and into the first portion of the cap member.

23. A polyaxial bone anchoring device comprising:
- a receiving part configured to be pivotably connected to a head of an anchoring element, the receiving part having a first end, a second end, a central axis extending through the first end and the second end, a channel intersecting the central axis for receiving a rod, an accommodation space for accommodating the head, the accommodation space having an opening at the second end, and a passage extending along the central axis from the first end to the accommodation space;
- a cap member having a first portion configured to be positioned in the accommodation space and to hold the head, wherein the first portion is expandable in the accommodation space to allow insertion of the head and compressible to exert pressure on the head; and
- a sleeve-like insert piece comprising a spherical segment-shaped outer surface portion, wherein the insert piece is configured to be positioned at least partially around the first portion of the cap member and to pivot in the receiving part when the cap member and the insert piece are in the receiving part;
- wherein the first portion of the cap member has a hollow interior space for accommodating the head and an opening for inserting the head, and wherein the opening of the cap member has a bounding edge having an asymmetry relative to the central axis to permit the head to pivot at a greater angle in one direction relative to the central axis compared to other directions relative to the central axis.

24. A polyaxial bone anchoring device comprising:
- an anchoring element, wherein the anchoring element comprises a shank for anchoring in the bone and a head comprising a spherical segment-shaped outer surface;
- a receiving part configured to be pivotably connected to the head of the anchoring element, the receiving part having a first end, a second end, a central axis extending through the first end and the second end, a channel intersecting the central axis for receiving a rod, an accommodation space for accommodating the head, the accommodation space having an opening at the second end, and a passage extending along the central axis from the first end to the accommodation space;
- a cap member having a first portion configured to be positioned in the accommodation space and to hold the head, wherein the first portion is expandable in the accommodation space to allow insertion of the head and compressible to exert pressure on the head; and
- a sleeve-like insert piece comprising a spherical segment-shaped outer surface portion, wherein the insert piece is configured to be positioned at least partially around the first portion of the cap member and to pivot in the receiving part when the cap member and the insert piece are in the receiving part;
- wherein when the cap member and the insert piece are in the receiving part and the head of the anchoring element is inserted in the cap member, the receiving part, the insert piece, and the anchoring element are pivotable relative to one another, and wherein the anchoring element and the insert piece are configured to be locked at respective angles relative to the central axis of the receiving part by exerting pressure with the cap member on the head and the insert piece.

* * * * *